United States Patent [19]

Tezuka et al.

[11] Patent Number: 4,715,942

[45] Date of Patent: Dec. 29, 1987

[54] ELECTROPHORESIS APPARATUS

[75] Inventors: Sigeru Tezuka; Shoichi Yamamoto; Masayoshi Yamamoto, all of Saitama, Japan

[73] Assignee: Fuji Photo Film Co., Ltd., Kanagawa, Japan

[21] Appl. No.: 12,402

[22] Filed: Feb. 9, 1987

[30] Foreign Application Priority Data

Feb. 7, 1986 [JP] Japan .................................. 61-25587

[51] Int. Cl.[4] ........................................... G01N 27/28
[52] U.S. Cl. ............................. 204/299 R; 204/182.8
[58] Field of Search ............. 204/299 R, 182.8, 182.9, 204/301

[56] References Cited

U.S. PATENT DOCUMENTS

| | | | |
|---|---|---|---|
| 4,142,960 | 3/1979 | Hahn et al. | 204/182.8 X |
| 4,325,796 | 4/1982 | Hoefer et al. | 204/299 R X |
| 4,518,476 | 5/1985 | Delony et al. | 204/182.8 X |
| 4,576,693 | 3/1986 | Kreisher et al. | 204/299 R X |

FOREIGN PATENT DOCUMENTS 0113700  7/1984  European Pat. Off. .

Primary Examiner—John F. Niebling
Assistant Examiner—John S. Starsiak, Jr.
Attorney, Agent, or Firm—Sughrue, Mion, Zinn, Macpeak & Seas

[57]  ABSTRACT

An apparatus for conducting electrophoresis is fabricated by use of an electrophoresis sheet composed of two sheet members consisting of a non-conductive organic polymer film and disposed to stand facing each other, spacers having predetermined thicknesses disposed between the two sheet members at right and left edge portions, and an electrophoresis gel membrane of a uniform thickness grasped between the two sheet members. The apparatus is provided with a pair of flat plate-like supporting members for supporting the electrophoresis sheet by sandwiching it therebetween, and a spacer disposed between the electrophoresis sheet and at least one of the flat plate-like supporting members, and contacting edge portions of the electrophoresis sheet.

6 Claims, 4 Drawing Figures

ELECTROPHORESIS APPARATUS

BACKGROUND OF THE INVENTION

1. Field of the Invention

This invention relates to an electrophoresis apparatus used for separation, analysis or the like of a substance having an electrically dissociated group in a solution, like protein or nucleic acid, on the basis of a difference in the electric charge and molecular weight of the particles.

2. Description of the Prior Art

There has heretofore been known an operation of electrophoresis by which separation of a substance by utilizing migration of charged molecules or particles of protein, nucleic acid, their decomposition product, or the like, is effected in a sheet-like supporting medium such as a gel membrane or a filter paper impregnated with a buffer solution under the effect of an electric field. The electrophoresis is utilized particularly for separation and fixation of the high molecular weight substances of the living body as mentioned above.

Particularly, in the genetic engineering which has attracted attention in recent years, the electrophoresis operation is indispensable for determining base arrangement in the molecule of nucleic acid such as DNA by utilizing autoradiography. In general, the electrophoresis operation for this purpose includes the step of subjecting a series of mixtures of base-specific reaction products of DNA or DNA fragments provided with a radioactive label to migration in the electric field within an electrophoresis supporting medium whereby the mixtures migrate parallel each other in the direction of the electric field. The migration pattern of multiple rows obtained after the migration (a group of zones formed by electrophoresis on the supporting medium) is recorded as an autoradiograph, and then the base arrangement is determined by comparing positions of the zones in the respective rows with each other. The comparison is carried out based on the electrophoresis principle that base-specific reaction products having equal molecular weights migrate to equal distance if the electrophoresis is started from the same line.

In general, filter paper, a membrane filter, a starch gel membrane, a polyacrylamide gel membrane or the like is used as the electrophoresis supporting medium in the form of a sheet having a uniform thickness. In the case where a gel membrane such as a starch gel membrane or a polyacrylamide gel membrane is used, the liquid for gel preparation has heretofore been introduced into a mold constituted by disposing a supporting frame (spacer) around a flat supporting member formed of a non-conductive material such as a glass plate, and gelled for use as the gel membrane, after the upper surface is enclosed by a different supporting member if necessary. However, this method of forming gel membrane is very troublesome as it requires complicated operations prior to the electrophoresis operation.

Accordingly, as disclosed in, for example, Japanese Unexamined Patent Publication No. 59(1984)-126237, the applicant proposed an electrophoresis sheet which requires no troublesome operations of gel preparation and is easy to use. The proposed electrophoresis sheet comprises two sheet members formed of a non-conductive organic polymer film and disposed to stand facing each other, spacers having predetermined thicknesses disposed at both edge portions between the two sheet members, and an electrophoresis gel membrane enclosed between the two sheet members in a uniform thickness. With the proposed electrophoresis sheet, since the gel membrane can be supplied in the form disposed between the two polymer films, the operators can purchase the electrophoresis sheets and easily conduct the electrophoresis operation.

The aforesaid electrophoresis sheet is used, as in the conventional method, in the arrangement so that the gel membrane extends vertically. Therefore, using said electrophoresis sheet, an electrophoresis apparatus provided with a pair of flat plate like supporting members (formed of glass plates, ceramic plates or the like) for supporting the flexible electrophoresis sheet in the form standing erect by sandwiching the sheet from both surfaces thereof is used. Electrophoresis is conducted by applying a gradient in potential in the vertical direction via a buffer solution according to the known method.

However, it was found that, in the case where the electrophoresis sheet is supported by being sandwiched between the flat plate-like supporting members, the migration pattern is distorted even by very small dust or the like which may present between the electrophoresis sheet and the rigid supporting members. Specifically, when the electrophoresis sheet is supported as mentioned above, the gel membrane at the portion where the dust or the like is pushed against the polymer films is distorted together with the polymer film, and the thickness of the gel membrane varries at said portion. Therefore, the migration speed of charged substances under electrophoresis becomes uneven while they pass through the portion where the thickness of the gel membrane is uneven. As a result, distortion of migration pattern such as oblique, bend or zigzag distortion arises. If the migration pattern is distorted, the migration pattern cannot be discriminated or the reading accuracy becomes low. In the case of the operation including the procedure of comparing multiple rows of migration pattern as in the operation for determining the base arrangement of DNA or the like, low accuracy of the migration pattern reading results in low reliability of the information obtained on the base sequence in nucleic acid or the like.

SUMMARY OF THE INVENTION

The primary object of the present invention is to provide an electrophoresis apparatus wherein electrophoresis is conducted without distortions of migration patterns by use of the aforesaid convenient electrophoresis sheet.

Another object of the present invention is to provide an electrophoresis apparatus which improves reliability of the information obtained by electrophoresis.

The preset invention provides an electrophoresis apparatus for conducting electrophoresis by use of an electrophoresis sheet composed of two sheet members formed of a non-conductive organic polymer film and disposed to stand facing each other, spacers having predetermined thicknesses disposed at both edge portions between the two sheet members, and an electrophoresis gel membrane of uniform thickness grasped between the two sheet members, wherein the improvement comprises the provision of:

(i) a pair of flat plate-like supporting members for supporting said electrophoresis sheet by sandwiching it therebetween, and (ii) a spacer disposed between said electrophoresis sheet and at least one of said flat plate-like supporting members, and contacting edge portions of said electrophoresis sheet.

With the electrophoresis apparatus in accordance with the present invention, the spacer disposed between the electrophoresis sheet and the flat plate-like supporting member reliably prevents the gel membrane of the electrophoresis sheet from being dimpled by dust or the like. Therefore, it is possible to prevent distortion of migration pattern caused by dimpling of the gel membrane, thus to improve reading accuracy of the migration pattern and to improve reliability of the information on base sequence or the like obtained by means of electrophoresis.

DESCRIPTION OF THE PREFERRED EMBODIMENTS

The present invention will hereinbelow be described in further detail with reference to the accompanying drawings.

Figure 1:
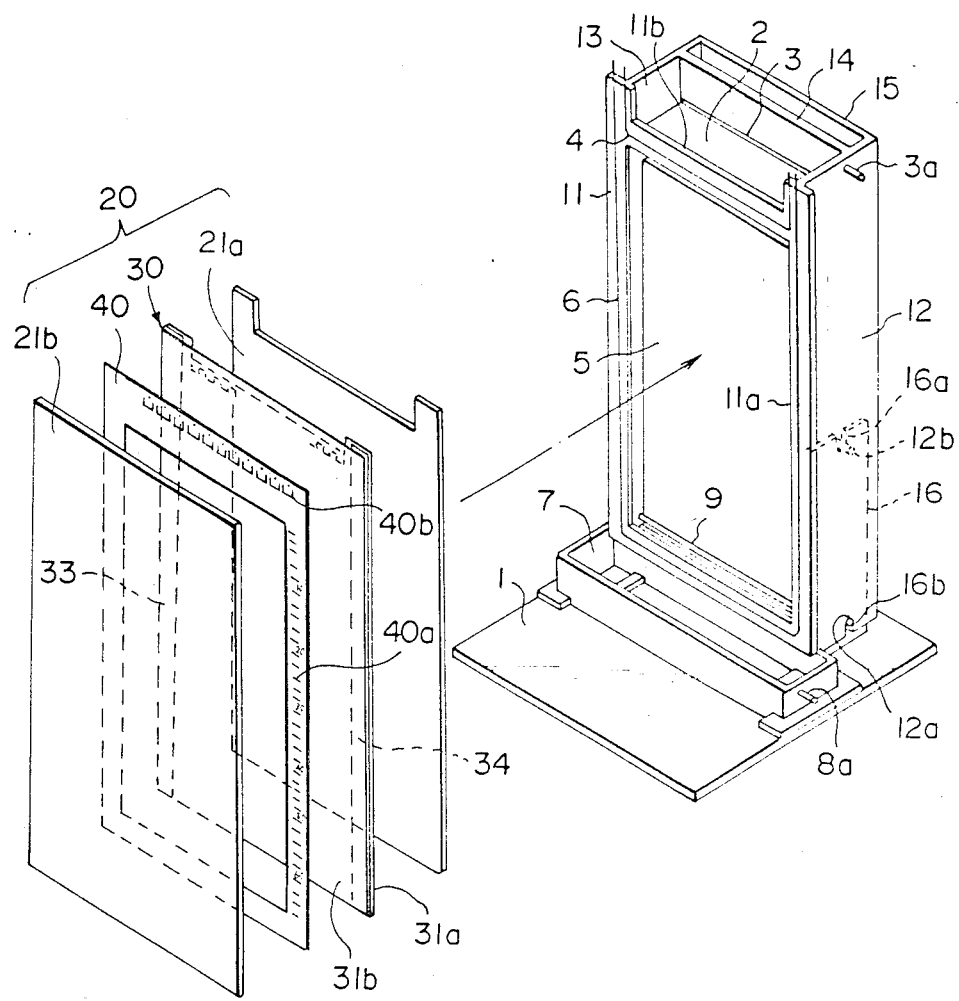
FIG. 1 is an exploded perspective view showing an embodiment of the electrophoresis apparatus in accordance with the present invention.
Figure 2:
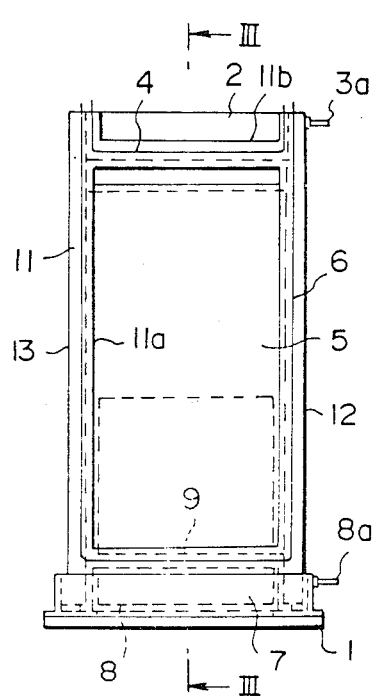
FIG. 2 is a front view showing the embodiment of FIG. 1.
Figure 3:
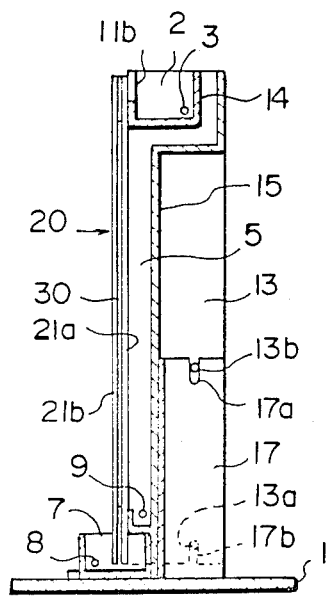
FIG. 3 is a sectional side view taken along line III—III of FIG. 2.

Referring to FIGS. 1, 2 and 3, the apparatus is basically composed of a supporting base 1, and an upper buffer solution vessel 2, a temperature holding water vessel 5, and a lower buffer solution vessel 7 which are mounted on the supporting base 1. An upper electrode 3 and a lower electrode 8 constituted by a single platinum wire extending in the width direction of the apparatus are respectively disposed in the upper buffer solution vessel 2 and the lower buffer solution vessel 7, so that the electrodes 3 and 8 are dipped in a buffer solution when the buffer solution is introduced into the upper buffer solution vessel 2 and the lower buffer solution vessel 7. The electrodes 3 and 8 are respectively connected to external terminals 3a and 8a projecting outwardly from the side walls of the upper buffer solution vessel 2 and the lower buffer solution vessel 7.

The upper buffer solution vessel 2 is defined by side plates 12 and 13, a rear and bottom plate 14, and a front frame 11, and is formed with the upper surface open. A cutaway portion 11b is formed at the upper section of the front frame 11. The temperature holding water vessel 5 extends from the rear of the upper buffer solution vessel 2 to the side under the upper buffer solution vessel 2, and downwardly near to the lower buffer solution vessel 7. The temperature holding water vessel 5 is defined by the side plates 12 and 13, a back plate 15 and the front frame 11. The side plates 12 and 13 and the front frame 11 are used commonly to the upper buffer solution vessel 2 and the temperature holding water vessel 5, and thus the upper buffer solution vessel 2 and the temperature holding water vessel 5 are formed integrally with each other. A front opening 11a is formed in the front surface of the temperature holding water vessel 5.

The upper buffer solution vessel 2 and the temperature holding water vessel 5 formed integrally with each other are held on the supporting base 1 so that the side plates 12 and 13 engage with a pair of vertical plates 16 and 17, which are secured to the upper surface of the supporting base 1, by grasping them from outside. Specifically, the engagement of the side plates 12 and 13 with the vertical plates 16 and 17 is effected as described below. First engagement grooves 12a and 13a which are opened downwardly are formed respectively at the lower ends of the side plates 12 and 13, and second engagement grooves 16a and 17a which are opened upwardly are respectively formed at the upper ends of the vertical plates 16 and 17. Second engagement pins 12b and 13b projecting inwardly for engaging with the second engagement grooves 16a and 17a are secured to the inner surfaces of the side plates 12 and 13. Also, first engagement pins 16b and 17b for engaging with the first engagement grooves 12a and 13a are secured to the outer surfaces of the vertical plates 16 and 17. Therefore, when the upper buffer solution vessel 2 and the temperature holding water vessel 5 formed integrally with each other are simply moved down so that the side plates 12 and 13 grasp the vertical plates 16 and 17 therebetween, the first engagement grooves 12a and 13a engage with the first engagement pins 16b and 17b, and the second engagement pins 12b and 13b engage with the second engagement grooves 16a and 17a. In this manner, the upper buffer solution vessel 2 and the temperature holding water vessel 5 formed integrally with each other are mounted on the supporting base 1. When the upper buffer solution vessel 2 and the temperature holding water vessel 5 are to be removed from the supporting base 1, they may merely be moved up from the supporting base 1. Thus mounting and removal of the upper buffer solution vessel 2 and the temperature holding water vessel 5 can be conducted very easily. The lower buffer solution vessel 7 is releasably held on the supporting base 1 at the position below the front frame 11.

As shown in FIG. 3, an electrophoresis sheet assembly 20 composed of flat plate-like supporting members 21a and 21b formed of glass plates, ceramic plates, or the like and an electrophoresis sheet 30 of the aforesaid type grasped between the flat plate-like supporting members 21a and 21b is fitted to the front side of the front frame 11, and then the upper buffer solution vessel 2 and the temperature holding water vessel 5 are mounted on the supporting base 1. As a result, the electrophoresis sheet assembly 20 closes the cutaway portion 11b in the front surface of the upper buffer solution vessel 2 and the front opening 11a of the temperature holding water vessel 5. In this case, a buffer solution vessel packing 4 and a water vessel packing 6 are provided on the front frame 11 so that the buffer solution and water do not leak between the contact surfaces of the electrophoresis sheet assembly 20 and the front frame 11.

Figure 4:
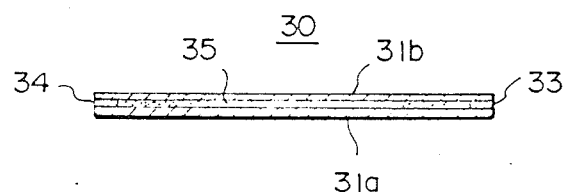
FIG. 4 is a sectional view showing the electrophoresis sheet used in the electrophoresis apparatus of the present invention.

The electrophoresis sheet assembly 20 will hereinbelow be described in detail. As shown in detail in FIG. 4, the electrophoresis sheet 30 is composed of sheet members 31a and 31b formed of a non-conductive organic polymer film and disposed to stand facing each other, spacers 33 and 34 having predetermined thicknesses and disposed at both the edge portions between the sheet members 31a and 31b, and an electrophoresis gel membrane 35 having a uniform thickness and grasped between the sheet members 31a and 31b. As the sheet members 31a and 31b, any material may be used insofar as it has good surface flatness and is non conductive and substantially impermeable to water. For this purpose, it is possible to use, for example, a polyester such as polyethylene terephthalate or polycarbonate of bisphenol A, polymethyl methacrylate, polyethylene, polystyrene, a vinyl polymer such as polyvinyl chloride, a polyamide such as nylon, or a copolymer of the monomers mentioned above, e.g. vinylidene chloride-vinyl chloride copolymer. The materials of the sheet members 31a and 32b may be identical or different. The front sheet member 31b (which is otherwise called the cover sheet) should preferably be as thin as practicable for enabling exposure for autoradiography therethrough. Thus the thickness of the front sheet member 31b is approximately 50 μm or less, preferably within the range of approximately 3 μm to approximately 50 μm, more preferably within the range of approximately 5 μm to approximately 40 μm. The thickness of the rear sheet member 31a may be equal to or different from the thickness of the front sheet member 31b, and may be within the range of approximately 5 μm to approximately 5 mm, preferably within the range of approximately 8 μm to approximately 3 mm.

The electrophoresis gel membrane 35 may be of any type insofar as electrophoresis can be effected therein and may be, for example, an acryl amide gel membrane, an agarose gel membrane, a starch gel membrane, an agar gel membrane, a cellulose acetate porous membrane, or filter paper.

The electrophoresis sheet 30 having the aforesaid configuration is grasped between the flat plate-like supporting members 21a and 21b. As shown in FIG. 1, as a requirement of the present invention, a square frame-like spacer 40 is disposed between the flat plate-like supporting member 21b farther from the front frame 11 and the electrophoresis sheet 30. The spacer 40 having this shape contacts only the edge portions of the electrophoresis sheet 30 when the electrophoresis sheet 30 is grasped between the flat plate-like supporting members 21a and 21b. Therefore, the center portion of the very thin and flexible sheet member 31b, i.e. the portion thereof facing the gel membrane 35 utilized for electrophoresis, is spaced from the supporting member 21b by a distance equal to the thickness of the spacer 40. The thickness of the spacer 40 should preferably be within the range of 0.15 mm to 0.6 mm, and may be 0.25 mm for example.

The flat plate-like supporting members 21a and 21b having the electrophoresis sheet 30 grasped therebetween are secured to the front frame 11 by use of, for example, clips. Then, a buffer solution is introduced into the upper buffer solution vessel 2 and the lower buffer solution vessel 7, and water is introduced into the temperature holding water vessel 5. A predetermined voltage is then applied across the external terminals 3a and 8a for carrying out electrophoresis. A cutaway portion like the cutaway portion 11b at the upper end of the front frame 11 is formed at the upper end of the supporting member 21a closer to the front frame 11, and the buffer solution in the upper buffer solution vessel 2 contacts the upper end of the gel membrane 35 via the cutaway portion. On the other hand, the lower end of the electrophoresis sheet assembly 20 is projected into the lower buffer solution vessel 7, so that the lower end of the gel membrane 35 contacts the buffer solution in the lower buffer solution vessel 7. Accordingly, the voltage applied across the external terminals 3a and 8a acts on the gel membrane 35 via the buffer solution, and electrophoresis of a substance such as protein or nucleic acid introduced from the upper end of the gel membrane 35 is carried out.

In this case, since the electrophoresis sheet assembly 20 closes the front opening 11a of the temperature holding water vessel 5, water in the temperature holding water vessel 5 contacts the electrophoresis sheet assembly 20 at said section, whereby the temperature of the electrophoresis sheet assembly 20 is made uniform. Therefore, the cooling (or temperature holding) effect on the gel membrane 35 becomes approximately uniform over the overall surface, and it is possible to prevent generation of a smiling effect, i.e. the effect that the migration speed of the charged substance becomes different between both ends of the gel membrane and the center thereof and the migration pattern is bent in a circular arc form.

As mentioned above, since the spacer 40 is disposed, the center of the thin and flexible sheet member 31b is slightly spaced from the supporting member 21b. Therefore, even though dust or the like is present on the surface of the sheet member 31b or on the surface of the supporting member 21b, there is no risk of the gel membrane 35 being dimpled by dust or the like. Accordingly, no distortion arises in the migration pattern, and the migration pattern can be read accurately.

In this embodiment, as shown in FIG. 1, a scale 40a for indicating the vertical distance and an indicator 40b for indicating the slot position are provided on the side portions of the spacer 40. Therefore, it is possible to visually measure the migration distance of the migration pattern by utilizing the scale 40a.

Before the electrophoresis sheet 30 is disposed between the flat plate-like supporting members 21a and 21b as mentioned above, water should preferably be applied to the inner surface of the supporting member 21a disposed closer to the front frame 11, i.e. the surface of the supporting member 21a on the side of the electrophoresis sheet 30. In this case, since the electrophoresis sheet 30 closely contacts the supporting member 21a over the overall surface, the cooling (or temperature holding) effect of water in the temperature holding water vessel 5 becomes more uniform over the overall surface of the gel membrane 35, and it is possible to prevent the smiling effect more reliably. Also, when the electrophoresis sheet 30 is closely contacted with the supporting member 21a, it is possible to prevent the buffer solution from entering therebetween, forming spots therebetween, and rendering the migration pattern unsuitable for reading. The spacer 40 having such effects is formed to a thickness of, for example, 0.25 mm.

In the aforesaid embodiment, since the temperature holding water vessel 5 is disposed on the rear side of the electrophoresis sheet 30, the rear sheet member 31a is closely contacted with the supporting member 21a, and the spacer 40 is disposed between the front sheet member 31b and the supporting member 21b. However, it is also possible to dispose the temperature holding water vessel 5 on the side of the electrophoresis sheet supporting member 21b, and to cool (or to hold the temperature of) the electrophoresis sheet 30 from its front side. In this case, the front sheet member 31b may be closely contacted with the supporting member 21b, and the spacer 40 may be disposed between the sheet member 31a and the supporting member 21a. Also, in the case where both sheet members 31a and 31b are formed to be very thin and cooling (or temperature holding) of the gel membrane 35 may be efficiently achieved by a means other than temperature holding water, the spacers may be disposed respectively on both surface sides of the electrophoresis sheet 30. Further, the temperature holding water vessel 5 may be omitted. In this case, the opening 11a of the front frame 11 may be omitted.

We claim:

1. An electrophoresis apparatus for conducting electrophoresis by use of an electrophoresis sheet composed of two sheet members formed of a non-conductive organic polymer film and disposed to stand facing each other, spacers having predetermined thicknesses disposed at right and left edge portions between the two sheet members, and an electrophoresis gel membrane of uniform thickness grasped between the two sheet members, wherein the improvement comprises the provision of:
(i) a pair of flat plate-like supporting members for supporting said electrophoresis sheet by sandwiching it therebetween, and
(ii) a spacer disposed between said electrophoresis sheet and at least one of said flat plate-like supporting members, and contacting edge portions of said electrophoresis sheet.

2. An apparatus as defined in claim 1 wherein said spacer disposed between at least one of said flat plate-like supporting members and said electrophoresis sheet has a thickness within the range of 0.15 mm to 0.6 mm.

3. An apparatus as defined in claim 2 wherein said spacer disposed between at least one of said flat plate-like supporting members and said electrophoresis sheet has a thickness of 0.25 mm.

4. An apparatus as defined in claim 1 wherein said spacer disposed between at least one of said flat plate-like supporting members and said electrophoresis sheet has a square frame-like shape.

5. An apparatus a defined in claim 1 wherein said spaoer disposed between at least one of said flat plate-like supporting members and said electrophoresis sheet is provided with a scale for indicating a vertical distance and an indicator for indicating a slot position, which are disposed at side portions of said spacer.

6. An apparatus as defined in claim 1 wherein the other of said flat plate-like supporting members has a cutaway portion at the upper end for allowing a buffer solution to contact the upper end of said electrophoresis gel membrane of said electrophoresis sheet.

* * * * *